United States Patent [19]

Sampson

[11] Patent Number: 4,949,733

[45] Date of Patent: Aug. 21, 1990

[54] NASAL OXYGEN CANNULA PAD

[76] Inventor: Robert D. Sampson, 3610 Chestnut, Kansas City, Mo. 64110

[21] Appl. No.: 222,631

[22] Filed: Jul. 21, 1988

[51] Int. Cl.⁵ ............................................ A61M 16/00
[52] U.S. Cl. ................................................... 128/864
[58] Field of Search ...................... 128/200.11, 200.14, 128/200.17, 200.18, 201.14, 207.17, 207.18, 206.13, 858, DIG. 26; 351/122; 604/174, 179, 180

[56] References Cited

U.S. PATENT DOCUMENTS

| | | | |
|---|---|---|---|
| 2,281,181 | 4/1942 | Clarke | 128/206.13 |
| 2,294,840 | 9/1942 | Dunn | 351/122 |
| 2,502,734 | 4/1950 | Lyons | 351/122 |
| 3,713,448 | 1/1973 | Arrott | 128/207.17 |
| 4,139,281 | 2/1979 | Luttner | 351/123 |
| 4,579,120 | 4/1986 | MacGregor | 604/174 |
| 4,632,670 | 12/1986 | Mueller, Jr. | 128/DIG. 26 |
| 4,699,139 | 10/1987 | Marshall et al. | 128/207.18 |

Primary Examiner—Robert A. Hafer
Assistant Examiner—C. Sam
Attorney, Agent, or Firm—Litman, McMahon & Brown

[57] ABSTRACT

An elongated cylinder of yieldable material is longitudinally slit in the shape of a "T", whereby it is easily mounted on nasal cannula tubing by lateral pressure and adjusted to the area where the tubing passes about the ears, functioning as a pad and helping to prevent local skin irritation.

9 Claims, 1 Drawing Sheet

NASAL OXYGEN CANNULA PAD

BACKGROUND OF THE INVENTION

In providing oxygen and/or other gases for medicinal purposes, nasal cannula are often used in hospitals and other health care institutions. Such cannula normally consist of a nose piece having stub tubing outlets through which the gas is fed directly into nasal passages. The nose piece receives the gas from flexible plastic tubing which usually extends rearwardly from the nose and about the ears to hold the cannula in place. The tubing normally passes between the upper ear flap and temple in the manner of common spectacles, whereby the cannula is relatively stable, even upon sliding movement of the patient's head on a pillow.

Typically, after the cannula is in place for several hours or days, skin irritation begins to appear where the tubing presses against the skin, at the points of greater pressure, i.e., between the upper ear and adjacent temple. The irritation is apparently due both to chafing and the presence of perspiration which does not easily evaporate under the non-porous tubing.

One of the objects of the present invention is to provide a nasal cannula pad which is comprised of a porous, soft sponge-like material easily positioned to protect the skin at points where irritation can be expected and which thereby reduces the likelihood of discomfort.

Another object is to provide such a cannula pad which allows ventilation to occur over the area of skin contact, thereby allowing perspiration to evaporate and further reducing the chances of irritation due to the cannula being in functional position over a long period of time.

A further object is to provide such a cannula pad which can be easily mounted on the cannula tubing and thereafter adjusted to a position where it can be of maximum benefit.

A still further object of this invention is to provide such a cannula pad whereby adequate retention on the tubing occurs without the need for adhesives, bands, ties, or other securing means.

A yet further object of the present invention is to provide a padded cannula which is highly effective for its intended purpose and yet inexpensive to produce and market.

Other objects and advantages of this invention will become apparent from the following description taken in connection with the accompanying drawings wherein are set forth, by way of illustration and example, certain embodiments of this invention.

SUMMARY OF THE INVENTION

Generally stated, this invention contemplates a nasal gas dispensing cannula pad adapted for mounting on plastic tubing of the cannula in the area adjacent the ears of the wearer. The pad is preferably in the shape of an elongated cylinder and contains a longitudinal slit or cut extending internally therealong which, in a preferred form, has the cross-sectional configuration of a "T". The lower point of the "T" forms an access opening along the surface of the pad and the cross of the "T" is entirely contained within the pad. In one example, the pad is approximately ⅝" in diameter and 3" long, with the cross of the "T" being radially centered and approximately 5/16" in transverse dimension. The stem of the "T" extends from approximately the radial center of the pad and at right angles to the "T", projecting radially through to the cylindrical surface. In this configuration, the pad is easily laterally slipped onto the tubing and adjustable longitudinally therealong.

DESCRIPTION OF THE PREFERRED EMBODIMENT

Figure 1:
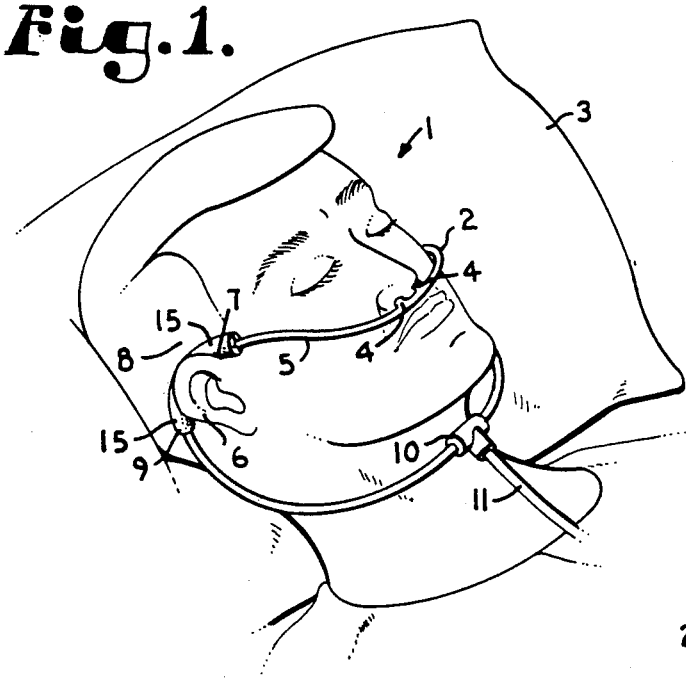
FIG. 1 is a perspective view showing the head of a person resting on a pillow with a nasal cannula in operable position and a pad embodying this invention covering the cannula tubing in the area about the person's ears.

Referring to the drawings for an illustrative embodiment of this invention, reference numeral 1 indicates a reclining person wearing a typical nasal cannula 2. The person is shown resting on a pillow 3, which occasionally may contact the cannula, tending to move it out of operable position as normal changes of position are made during sleeping and waking periods.

The cannula tube 2 includes nasal entry stubs 4, partially inserted into the nostrils and tubing 5 which bends about the upper portion of the ears 6, resting in the trough 7 formed between the upper portion of the ear 6 and the adjacent part of the temple 8. The tubing 5, as it extends about and behind the ear, is bent downwardly into a partial loop 9. The loop 9 terminates in a connector 10, which engages a feeder hose 11.

The tubing 5 in the area of the ear 6, and in absence of the pad of this invention, would be in relatively constant contact with the skin in the area of the trough 7. Over a period of time, this tends to cause discomfort due to irritation and inflammation. In order to reduce this tendency, a pad 15 embodying this invention is provided.

Figure 2:
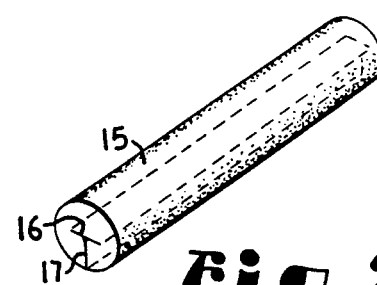
FIG. 2 is a perspective view showing the pad, on a larger scale than FIG. 1, and illustrating a "T" slit in broken lines extending internally therealong.
Figure 3:
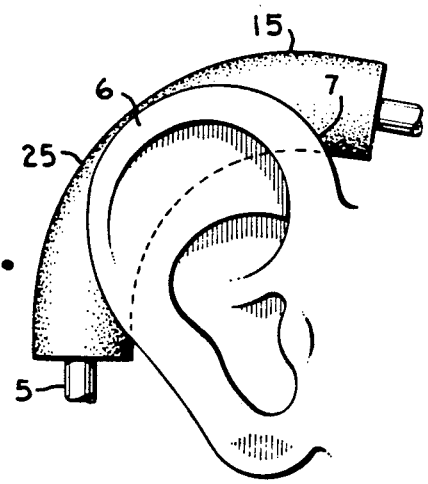
FIG. 3 is a fragmentary view in side elevation, on a larger scale than FIG. 2, showing the tube with the pad mounted thereon, both tube and pad bending about the base between the temple and the upper portion of the ear.
Figure 5:
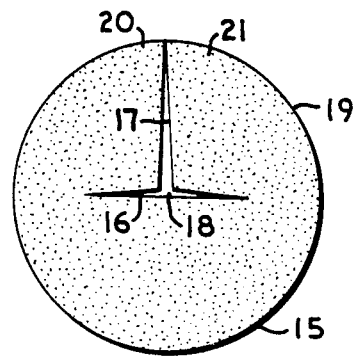
FIG. 5 is an end elevational view on a larger scale than FIG. 4 showing the pad with the "T" slit therein.
Figure 6:
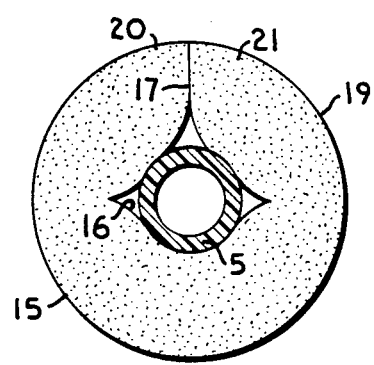
FIG. 6 is a view similar to FIG. 5 but showing the tube contained within the pad.

The pad 15, in this example, is of cylindrical shape, as best illustrated in FIGS. 2, 5 and 6, and is constructed of a soft foam-like material. A desirable material for this purpose is commonly known in the industry as flexible, open celled, ether-based, polyurethane foam having a 25 percent indentation force deflection. It is technically defined as a "15-100" foam. This designation uses, as the unit base, the number of pounds distributed over a standard area, in this instance, 15 pounds distributed over an area of 50 square inches at a 4" thickness. The cells are preferably approximately 35 to the inch.

The pad 15, in this example, is approximately ⅝" in diameter and includes a central slit 16 therein, roughly 5/16" in width and extending generally coaxially longitudinally through the entire length thereof. The length, in this embodiment, is approximately 3", however, such dimensions can vary without departing from the spirit of this invention.

A second slit 17 extends both longitudinally and radially along the pad 15 and intersects at 18 with the slit 16 at approximately the longitudinal axis of the pad 15. The slit 17 extends to and through the surface 19 of the pad 15 and thus provides direct lateral access into the slit 16 from the exterior of the pad 15 by resiliently spreading apart the opposed surfaces of the slit 17. The slits 16 and 17 are desirably normal to each other, that is, extending at right-angles in cross-section, and are mutually positioned so that the slit 17 tends to bisect the slit 16 in the cross-sectional center of the pad 15.

Figure 4:
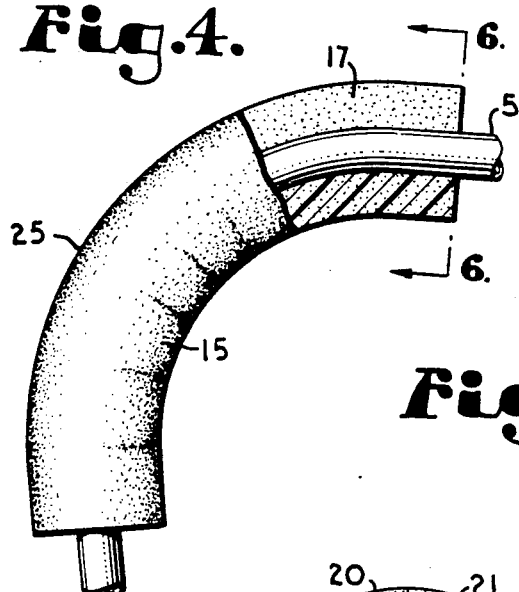
FIG. 4 is a fragmentary elevational view, on a scale larger than FIG. 3, showing the curved tube and pad, with a portion of the pad broken away to reveal the tube therein.

In order to conveniently mount the pad 15 on the cannula tubing 5, it is only necessary to either pull apart the sections 20 and 21 of the pad, which are adjacent to the slit 17, or directly urge the tube laterally into the slit 17. The tubing 5 is thus easily inserted completely into the radial center portion of the pad. Upon release of any spread force on the slit 17, the resiliency of the material functions to close the outer portion of the slit 17, thus causing the sections 20 and 21 to re-engage each other as the pad easily accommodates and surrounds the portion of the tubing 5 therewithin, FIGS. 4 and 5. Thus, the tubing becomes adequately secured within the pad.

The pad 15 may easily be adjusted along the tubing to a desired position where it rests in desired location about the ear, approximately as shown in FIG. 1. Further, by rotating the pad 15 about its axis so that the slit 17 faces outwardly or upwardly with respect to the ear 6, FIG. 1, the pad may easily be bent to a desired curve 25 without creating a tendency for the tubing 5 to exit laterally through the slit 17.

The pad 15, as described, comprises an easily mounted barrier between the tubing 5 and the skin trough between the upper portion of the ear 6 and the temple 8, thereby substantially reducing the chances of irritation, inflammation and consequent discomfort to a person wearing a nasal cannula.

It is to be understood that while one form of this invention has been illustrated and described, it is not to be limited thereto except insofar as such limitations are included in the following claims.

What is claimed and desired to be secured by Letters Patent is as follows:

1. In combination with a tube cannula, a pad for cushioning tubing contact area with skin surface and thereby reducing the likelihood of irritation comprising:
   (a) a flexible pad of generally continuous cross-section and
   (b) multiple slits intersecting generally centrally of said cross-section and forming an opening extending along and within said pad, said pad receiving said tube cannula into said opening;
   (c) one of said slits extending from the central portion of said pad to an exterior surface thereof;
   (d) said pad being located with respect to said tube cannula for preventing contact between said tube cannula and exposed skin of a person wearing said tube cannula.

2. For use with a nasal gas cannula having tubing, an ear pad for cushioning each contact area with said tubing and thereby reducing the likelihood of irritation comprising:
   (a) an elongated pad of generally continuous cross-section and formed of flexible material;
   (b) multiple slits intersecting generally centrally of said cross-section and forming an opening extending along and within said pad;
   (c) one of said slits extending from the central portion of said pad to an exterior surface thereof;
   (d) whereby the portion of cannula tubing which normally fits about the ear is laterally receivable within said pad;
   (e) said pad being of sufficient dimension with regard to said tubing to provide adequate cushioning between skin and said tubing.

3. The pad as set forth in claim 2 wherein said multiple slits are in the form of a "T".

4. The pad as set forth in claim 2 wherein:
   (a) said pad is formed of flexible, open-celled ether-based polyurethane foam having an indentation force deflection of 15 based upon a weight of 15 pounds distributed over an area of 50 square inches at 4" thickness and 25 percent indentation force deflection.

5. The pad as set forth in claim 2 wherein:
   (a) said opening is in the form of a "T" with said slit being the stem thereof.

6. The cushion as set forth in claim 4 wherein said pad has cells which are approximately 35 to the inch.

7. The pad as set forth in claim 2 wherein:
   (a) the pad is cylindrical in shape and approximately ⅜" in diameter and about 3" long.

8. The pad as set forth in claim 5 wherein:
   (a) the stem of said "T" extends from approximately the radial center of the pad.

9. The pad as set forth in claim 8 wherein:
   (a) said pad is in cylindrical form, about ⅜" in diameter and the cross of said "T" is approximately 5/16" in transverse dimension.

* * * * *